United States Patent [19]
Husain et al.

[11] Patent Number: 5,254,792
[45] Date of Patent: Oct. 19, 1993

[54] ISOPARAFFIN:OLEFIN ALKYLATION IN THE PRESENCE OF SYNTHETIC POROUS MCM-49

[75] Inventors: Altaf Husain, Marlton, N.J.; Albin Huss, Jr., Chadds Ford, Pa.; Donald J. Klocke, Somerdale; Hye K. C. Timken, Woodbury, both of N.J.

[73] Assignee: Mobil Oil Corporation, Fairfax, Va.

[21] Appl. No.: 774,482

[22] Filed: Oct. 10, 1991

[51] Int. Cl.$^5$ ............................................. C07C 2/56
[52] U.S. Cl. ................................ 585/722; 585/726
[58] Field of Search ............................ 585/722, 726

[56] References Cited

U.S. PATENT DOCUMENTS

| | | | |
|---|---|---|---|
| 3,549,557 | 12/1970 | Bolton et al. | 252/455 |
| 3,624,173 | 11/1971 | Kirsch | 260/671 |
| 3,644,564 | 2/1972 | Zwet et al. | 260/683.15 |
| 3,647,916 | 3/1972 | Caesar et al. | 260/683.43 |
| 3,655,813 | 4/1972 | Kirsch et al. | 260/683.43 |
| 3,706,814 | 12/1972 | Kirsch et al. | 260/683.43 |
| 3,738,977 | 6/1973 | Biale | 260/94.9 |
| 3,865,894 | 2/1975 | Kirsch et al. | 260/683.43 |
| 3,893,942 | 7/1975 | Yang | 252/411 |
| 3,917,738 | 11/1975 | Fenske et al. | 260/683.43 |
| 4,377,721 | 3/1983 | Chester et al. | 585/722 |
| 4,384,161 | 5/1983 | Huang | 585/722 |
| 4,439,409 | 3/1984 | Puppe et al. | 423/328 |
| 4,826,667 | 5/1989 | Zones et al. | 423/277 |
| 4,954,325 | 9/1990 | Rubin et al. | 423/328 |
| 4,981,663 | 1/1991 | Rubin | 423/277 |
| 4,992,615 | 2/1991 | Huss, Jr. et al. | 585/726 |
| 5,021,141 | 6/1991 | Rubin | 208/46 |

FOREIGN PATENT DOCUMENTS 0231860 8/1987 European Pat. Off. .
0293032 11/1988 European Pat. Off. .

*Primary Examiner*—Asok Pal
*Attorney, Agent, or Firm*—A. J. McKillop; D. P. Santini; R. B. Furr, Jr.

[57] ABSTRACT

The invention provides an isoparaffin: olefin alkylation process comprising contacting isoparaffin and olefin with a synthetic porous crystalline material which is characterized, in its uncalcined form, by an X-ray diffraction pattern including values substantially as set forth in Table I of the specification and having a composition comprising the molar relationship $$X_2O_3:(n)YO_2,$$

wherein n is less than about 20, X is a trivalent element and Y is a tetravalent element.

22 Claims, 3 Drawing Sheets

ISOPARAFFIN:OLEFIN ALKYLATION IN THE PRESENCE OF SYNTHETIC POROUS MCM-49

FIELD OF THE INVENTION

The present invention relates to an isoparaffin-olefin alkylation process carried out in the presence of a synthetic porous crystalline material to provide an alkylate product useful, inter alia, as an octane enhancer for gasoline.

BACKGROUND OF THE INVENTION

As a result of the curtailment in the use of tetraethyl lead as an octane-improving additive for gasoline, not only has the production of unleaded gasoline increased but the octane number specification of all grades of gasoline have increased as well. Isoparaffin-olefin akylation is a key route to the production of highly branched paraffin octane enhancers which are to be blended into gasolines.

Alkylation involves the addition of an alkyl group to an organic molecule. Thus, an isoparaffin can be reacted with an olefin to provide an isoparaffin of higher molecular weight. Industrially, alkylation often involves the reaction of $C_2$-$C_5$ olefins with isobutane in the presence of an acidic catalyst. Alkylates are valuable blending components for the manufacture of premium gasoline due to their high octane ratings.

In the past, alkylation processes have included the use of hydrofluoric acid or sulfuric acid as catalysts under controlled temperature conditions. Low temperatures are utilized in the sulfuric acid process to minimize the undesirable side reaction of olefin polymerization and the acid strength is generally maintained at 88-94 percent by the continuous addition of fresh acid and the continuous withdrawal of spent acid. The hydrofluoric acid process is less temperature-sensitive and the acid is easily recovered and purified.

The typical types of alkylation currently used to produce high octane gasoline blending component (processes such as hydrofluoric acid and sulfuric acid alkylation) have inherent drawbacks including acid consumption and disposal of corrosive materials. With the increasing demands for octane and the increasing environmental concerns, it has been desirable to develop an alkylation process based on a solid catalyst system. The catalyst of the present invention offers a refiner a more environmentally acceptable alkylation process than the currently used hydrofluoric and sulfuric acid alkylation processes.

Crystalline metallosilicates, or zeolites, have been widely investigated for use in the catalysis of isoparaffin alkylation. For example, U.S. Pat. No. 3,251,902 describes the use of a fixed bed of ion-exchanged crystalline aluminosilicate having a reduced number of available acid sites for the liquid phase alkylation of $C_4$-$C_{20}$ branched-chain paraffins with $C_2$-$C_{12}$ olefins. The patent further discloses that the $C_4$-$C_{20}$ branched-chain paraffin should be allowed to substantially saturate the crystalline aluminosilicate before the olefin is introduced to the alkylation reactor.

U.S. Pat. No. 3,450,644 discloses a method for regenerating a zeolite catalyst used in hydrocarbon conversion processes involving carbonium ion intermediates.

U.S. Pat. No. 3,549,557 describes the alkylation of isobutane with $C_2$-$C_3$ olefins using certain crystalline aluminosilicate zeolite catalysts in a fixed, moving or fluidized bed system, the olefin being preferably injected at various points in the reactor.

U.S. Pat. No. 3,644,564 discloses the alkylation of a paraffin with an olefin in the presence of a catalyst comprising a Group VIII noble metal present on a crystalline aluminosilicate zeolite, the catalyst having been pretreated with hydrogen to promote selectivity.

U.S. Pat. No. 3,647,916 describes an isoparaffin-olefin alkylation process featuring the use of an ion-exchanged crystalline aluminosilicate, isoparaffin/olefin mole ratios below 3:1 and regeneration of the catalyst.

U.S. Pat. No. 3,655,813 discloses a process for alkylating $C_4$-$C_5$ isoparaffins with $C_3$-$C_9$ olefins using a crystalline aluminosilicate zeolite catalyst wherein a halide adjuvant is employed in the alkylation reactor. The isoparaffin and olefin are introduced into the alkylation reactor at specified concentrations and catalyst is continuously regenerated outside the alkylation reactor.

U.S. Pat. No. 3,893,942 describes an isoparaffin alkylation process employing, as catalyst, a Group VIII metal-containing zeolite which is periodically hydrogenerated with hydrogen in the gas phase to reactivate the catalyst when it has become partially deactivated.

U.S. Pat. No. 3,236,671 discloses the use, in alkylation, of crystalline aluminosilicate zeolites having silica to alumina mole ratios above 3 and also discloses the use of various metals exchanged and/or impregnated on such zeolites.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc.

U.S. Pat. No. 3,624,173 discloses the use, in isoparaffin-olefin alkylation, of zeolite catalysts containing gadolinium.

U.S. Pat. No. 3,738,977 discloses alkylation of paraffins with ethylene employing a zeolite catalyst which possesses a Group VIII metal component, the catalyst having been pretreated with hydrogen.

U.S. Pat. No. 3,865,894 describes the alkylation of $C_4$-$C_6$ isoparaffin with $C_3$-$C_9$ monoolefin employing a substantially anhydrous acidic zeolite, for example acidic zeolite Y (zeolite HY), and a halide adjuvant.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone after which the reactants are passed concurrently with the catalyst so that a controlled amount of olefin is absorbed onto the catalyst before the combination of reactants and catalyst is introduced into an alkylation zone. This controlled olefin adsorption is said to prevent polymerization of the olefin during alkylation.

U.S. Pat. No. 4,377,721 describes an isoparaffin- olefin aklylation process utilizing, as catalyst, ZSM-20, preferably HZSM-20 or rare earth cation-exchanged ZSM-20.

U.S. Pat. No. 4,384,161 describes a process of alkylating isoparaffins with olefins to provide alkylate employing as catalyst a large pore zeolite capable of absorbing 2,2,4-trimethylpentane, e.g., ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large pore zeolite in combination with a Lewis acid in accordance with this patent is reported to greatly increase the acidity and selectivity of the zeolite thereby effecting alkylation with high olefin space velocity and low isoparaffin/olefin ratio.

U.S. Pat. No. 4,992,615 to Huss, Jr. et al. teaches isoparaffin: olefin alkylation in the presence of a synthetic porous crystalline material designated as MCM-22.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g. $AlO_4$, in which the tetrahedra are cross-linked by the sharing of oxygen atoms whereby the ratio of the total Group IIIA element, e.g. aluminum, and silicon atoms to oxygen atoms is 1:2. The electrovalence of the tetrahedra containing the Group IIIA element, e.g. aluminum, is balanced by the inclusion in the crystal of a cation, for example an alkali metal or an alkaline earth metal cation. This can be expressed wherein the ratio of the Group IIIA element, e.g. aluminum, to the number of various cations, such as $Ca/2$, $Sr/2$, $Na$, $K$ or $Li$, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449), zeolite ZSM-20 (U.S. Pat. No. 3,972,983); ZSM-35 (U.S. Pat. No. 4,016,245); zeolite ZSM-23 (U.S. Pat. No. 4,076,842); zeolite MCM-22 (U.S. Pat. No. 4,954,325); and zeolite MCM-35 (U.S. Pat. No. 4,981,663), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques.

U.S. Pat. No. 3,941,871 (U.S. Pat. No. Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicate of varying alumina and metal content.

U.S. Pat. No. 4,439,409 refers to a composition of matter named PSH-3 and its synthesis from a reaction mixture containing hexamethyleneimine. A composition of matter appearing to be identical to the PSH-3 of U.S. Pat. No. 4,439,409, but with additional structural components, is taught in European Patent Application 293,032. Hexamethyleneimine is also used for synthesis of MCM-22 in U.S. Pat. No. 4,954,325; MCM-35 in U.S. Pat. No. 4,981,663; and a ZSM-12 material in U.S. Pat. No. 5,021,141. A composition of matter referred to as zeolite SSZ-25 is taught in U.S. Pat. No. 4,826,667 and European Patent Application 231,860, said zeolite being synthesized from a reaction mixture containing an adamantane quaternary ammonium ion.

SUMMARY OF THE INVENTION

The present invention is directed to a process for isoparaffin: olefin alkylation in the presence of novel composition of a porous crystalline material named MCM-49. The uncalcined form of the porous crystalline material useful in the invention is readily identified and distinguished from other crystalline materials by its characteristic X-ray diffraction pattern. Additionally, the calcined form of the porous crystalline material of the invention is characterized by a bulk silica to alumina molar ratio ($SiO_2:Al_2O_3$) of less than about 24:1, preferably less than about 20:1. The calcined form of the porous crystalline material useful in the present invention transforms to a material having an X-ray diffraction pattern not readily distinguishable from that of calcined crystalline material MCM-22, as described in U.S. Pat. No. 4,954,325. In accordance with the invention, it has been found that the novel porous crystalline material MCM-49 exhibits surprising activity and longevity for isoparaffin:olefin alkylation. The instant crystalline material does not appear to contain all the components apparently present in the PSH-3 compositions described in U.S. Pat. No. 4,439,409. The composition of this invention is not contaminated with ZSM-12 or ZSM-5. The calcination transformation product exhibits unusual sorption capacities and unique catalytic utility when compared to the PSH-3 compositions synthesized in accordance with U.S. Pat. No. 4,439,409. As noted above, the MCM-49 material of the invention exhibits unique utility for catalytic alkylation when compared to MCM-22 synthesized as taught in U.S. Pat. No. 4,954,325.

DETAILED DESCRIPTION

Feedstocks

Figure 1:
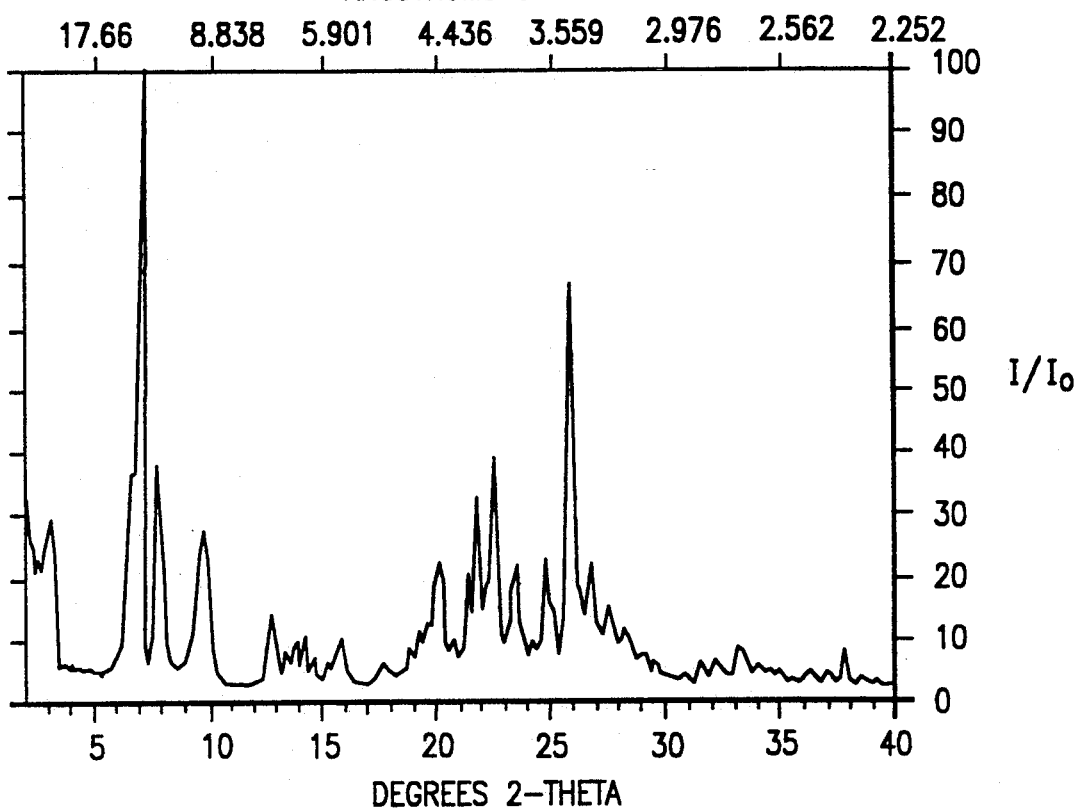
FIGS. 1-5 are X-ray diffraction patterns of the as-synthesized crystalline material products of Examples 1, 3, 5, 7 and 8, respectively, hereinafter presented.

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 20:1.

Process Conditions

The operating temperature of the alkylation process herein can extend over a fairly broad range, e.g., from about −25° C. to about 400° C., and is preferably within the range of from about 75° C. to about 200° C. The practical upper operating temperature will often be dictated by the need to avoid an undue occurrence of undesirable side reactions.

The pressures employed in the present process can extend over a considerably wide range, e.g., from subatmospheric pressure to about 5000 psig, and preferably from atmospheric pressure to about 1000 psig.

The amount of MCM-49 material used in the present alkylation process can be varied over relatively wide limits. In general, the amount of MCM-49 material as measured by the weight hourly space velocity (WHSV) based on olefin can range from about 0.01 to about 100 hr$^{-1}$, preferably from 0.04 to 10 hr$^{-1}$. It will, of course, be realized by those skilled in the art that the amount of catalyst selected for a particular reaction will be determined by several variables including the reactants involved as well as the nature of the catalyst and the operating conditions employed.

The isoparaffin reactant used in the present alkylation process is one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin reactant employed herein generally contains from 2 to about 12 carbon atoms. Representative examples are ethylene, propylene, butene-1, butene-2, isobutylene, pentenes, hexenes, heptenes and octenes. Particularly preferred are $C_3$ and $C_4$ olefins and mixtures thereof.

In general, the mole ratio of total isoparaffin to total olefin alkylating agent in the combined hydrocarbon feed can be from about 1:2 to about 1000:1 and is preferably in a range of from about 5:1 to about 100:1. The isoparaffin and/or olefin reactants can be in either the vapor phase or the liquid phase and can be neat, i.e., free from intentional admixture or dilution with other material, or the reactants can be brought into contact with the catalyst composition with the aid of carrier gases or diluents such as, for example, hydrogen or nitrogen.

The reactants can be introduced to the alkylation reaction zone together with one or more other materials which serve to enhance the overall conversion operation. Thus, for example, relatively small quantities of hydrogen and/or hydrogen donors can be present in the reaction zone to suppress catalyst aging. Water and/or materials such as alcohols which provide water under the alkylation conditions selected can also be introduced into the reaction zone for this purpose. Oxygen and/or other materials which tend to suppress oligomerization of the olefin feed can be present in the typically very small amounts which are effective to achieve this benefit. The optimum amounts of these optional materials which can be utilized to advantage in a particular alkylation operation can be readily determined by those skilled in the art employing routine experimentation.

The alkylation process of the present invention can be carried out as a batch-type, semi-continuous or continuous operation utilizing a fixed or moving bed of the MCM-49 catalyst component. A preferred embodiment entails use of a catalyst zone wherein the hydrocarbon charge is passed concurrently or countercurrently through a moving bed of particle-form catalyst. The latter, after use, is conducted to a regeneration zone where coke is removed, e.g., by burning in an oxygen-containing atmosphere (such as air) at elevated temperature or by extracting with a solvent, after which the regenerated catalyst is recycled to the conversion zone for further contact with the organic reactants.

Alkylation Catalyst

The alkylation catalyst useful in the present invention comprises a crystalline material which has a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than about 20, e.g. from 2 to less than about 20, usually from about 15 to less than about 20, more usually from about 16 to about 19. In the as-synthesized form, the material has a formula, on an anhydrous basis and in terms of moles of oxides per n moles of $YO_2$, as follows:

$$(0.1-0.6)M_2O:(1-4)R:X_2O_3:nYO_2$$

wherein M is an alkali or alkaline earth metal, and R is an organic moiety. The M and R components are associated with the material as a result of their presence during crystallization, and are easily removed by post-crystallization methods hereinafter more particularly described.

The crystalline material useful as a catalyst component in the invention is thermally stable and in the calcined form exhibits high surface area (greater than 400 m$^2$/gm) and unusually large sorption capacity when compared to previously described materials such as calcined PSH-3 and SSZ-25 having similar X-ray diffraction patterns. To the extent desired, the original sodium cations of the as-synthesized material can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which tailor the catalytic activity for certain hydrocarbon conversion reactions. These include hydrogen, rare earth metals and metals of Groups IIA, IIIA, IVA, IB, IIB, IIIB, IVB and VIII of the Periodic Table of the Elements.

In the as-synthesized form, the crystalline MCM-49 material which is useful as a catalyst component in the invention appears to be a single crystalline phase. It can be prepared in essentially pure form with little or no detectable impurity crystal phases and has an X-ray diffraction pattern which is distinguished from the patterns of other known as-synthesized or thermally treated crystalline materials by the lines listed in Table I below:

TABLE I

| Interplanar d-Spacing (A) | Relative Intensity, I/Io × 100 |
|---|---|
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

In its calcined form, the crystalline MCM-49 material useful as a catalyst component in the present invention transforms to a single crystal phase with little or no detectable impurity crystal phases having an X-ray diffraction pattern which is not readily distinguished from that of MCM-22, but distinguishable from the patterns of other known crystalline materials. The X-ray diffraction pattern of the calcined form of MCM-49 includes the lines listed in Table II below:

TABLE II

| Interplanar d-Spacing (A) | Relative Intensity, I/Io × 100 |
|---|---|
| 12.41 ± 0.24 | vs |
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step.

The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60–100), s=strong (40–60), m=medium (20–40) and w=weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-49 and MCM-22 in their as-synthesized form.

The crystalline material of the invention may be subjected to treatment to remove part or all of any organic constituent. The crystalline material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g. aluminum, is in the structure, impregnated therein or intimately physically admixed therewith. Such component can be impregnated in or on to it such as, for example, by, in the case of platinum, treating the silicate with a solution containing a platinum metal- containing ion. Thus, suitable platinum compounds for this purpose include chloroplatinic acid, platinous chloride and various compounds containing the platinum amine complex.

The above crystalline MCM-49 material is transformed to another form by thermal treatment. This transformation product exhibits unusual catalytic properties for isoparaffin:olefin alkylation in comparison with MCM-22, and may also be readily distinguished from MCM-22 by a comparison of the X-ray diffraction patterns of uncalcined MCM-22 and MCM-49. The terms "thermal treatment" and "calcining" are used interchangably herein to describe a step of heating the crystalline material to a temperature of at least about 370° C. Such thermal treatments are generally performed by heating at a temperature of at least about 370° C. for at least 1 minute and generally not longer than 20 hours at subatmospheric or atmospheric pressure.

The MCM-49 synthetic crystalline material of the invention, in its calcined form, is characterized by a bulk silica:alumina ($SiO_2:Al_2O_3$) molar ratio of less than about 24:1, preferably less than about 20:1.

The crystalline material useful as a catalyst constituent in the present invention, when employed either as an adsorbent or as a catalyst in an organic compound conversion process should be dehydrated, at least partially.

This can be done by heating to a temperature in the range of about 200° C. to less than about 370° C., preferably from about 200° C. to about 300° C., in an atmosphere such as air, nitrogen, etc. and at atmospheric, subatmospheric or superatmospheric pressures for between 30 minutes and 48 hours. Dehydration can also be performed at room temperature merely by placing the MCM-49 in a vacuum, but a longer time is required to obtain a sufficient amount of dehydration.

The present crystalline material useful as a catalyst constituent in the present inventive process can be prepared from a reaction mixture containing sources of alkali or alkaline earth metal (M), e.g. sodium or potassium, cation, an oxide of trivalent element X, e.g. aluminum, an oxide of tetravalent element Y, e.g. silicon, hexamethyleneimine directing agent (R), and water, said reaction mixture having a composition, in terms of mole ratios of oxides, within the following ranges:

| Reactants | Useful | Preferred |
| --- | --- | --- |
| $YO_2/X_2O_3$ | 12 to <30 | 18 to 28 |
| $H_2O/YO_2$ | 10 to 70 | 15 to 40 |
| $OH^-/YO_2$ | 0.05 to 0.50 | 0.05 to 0.30 |
| $M/YO_2$ | 0.05 to 3.0 | 0.05 to 1.0 |
| $R/YO_2$ | 0.2 to 1.0 | 0.3 to 0.5 |

In this synthesis method, if more than one X component is present, at least one must be present such that the $YO_2/X_2O_3$ molar ratio thereof is less than about 30. For example, if aluminum oxide and gallium oxide components are used in the reaction mixture, at least one of the $YO_2/Al_2O_3$ and $YO_2/Ga_2O_3$ molar ratios must be less than about 30. If only aluminum is present, the $YO_2/Al_2O_3$ ratio must be less than about 30.

The source of $YO_2$ may be soluble or insoluble, but is preferably comprised predominately of solid $YO_2$, for example at least about 30 wt. % solid $YO_2$ in order to obtain the crystal product of the invention. Where $YO_2$ is silica, the use of a silica source containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystalline MCM-49 formation from the above mixture. Preferably, therefore, the solid $YO_2$, e.g. silica, source contains at least about 30 wt. % solid $YO_2$, e.g. silica, and more preferably at least about 40 wt. % solid $YO_2$, e.g. silica.

Crystallization of the present crystalline material catalyst constituent can be carried out at either static or stirred condition in a suitable reactor vessel, such as for example, polypropylene jars or teflon lined or stainless steel autoclaves. The total useful range of temperatures for crystallization is from about 80° C. to about 225° C. for a time sufficient for crystallization to occur at the temperature used, e.g. from about 24 hours to about 60 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of the new crystals may be facilitated by the presence of at least 0.01 percent, preferably 0.10 percent and still more preferably 1 percent, seed crystals (based on total weight) of crystalline product. Useful seed crystals include MCM-22 and/or MCM-49.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In the case of many catalysts, it is desired to incorporate the crystalline material with another material resistant to the conditions employed in the alkylation process of the invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the crystalline material, i.e. combined therewith or present during synthesis of the new crystal, which is active, may change the conversion and/or selectivity of the catalyst under certain alkylation conversion conditions. Inactive materials suitably serve as diluents to control the amount of conversion so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for water, cyclohexane and/or n-hexane, they were Equilibrium Adsorption values determined as follows:

A weighed sample of the calcined adsorbant was contacted with the desired pure adsorbate vapor in an adsorption chamber, evacuated to less than 1 mm and contacted with 12 Torr of water vapor and 40 Torr of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. The new synthetic material of this invention always exhibits Equilibrium Adsorption values of greater than about 10 wt. % for water vapor, greater than about 4.3 wt. %, usually greater than about 7 wt. % for cyclohexane vapor and greater than about 10 wt. % for n-hexane vapor. These vapor sorption capacities are a notable distinguishing feature of the present crystalline material.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

A 1 part quantity of $Al_2(SO_4)_3 \cdot xH_2O$ was dissolved in a solution containing 1.83 parts of 50% NaOH solution and 13 parts of $H_2O$. To this were added 1.78 parts of hexamethyleneimine (HMI) followed by 6.6 parts of amorphous silica precursor (46% solids). The mixture was thoroughly mixed until uniform.

The reaction mixture had the following composition in mole ratios:

| | | |
|---|---|---|
| $SiO_2/Al_2O_3$ | = | 30 |
| $OH^-/SiO_2$ | = | 0.25 |
| $Na/SiO_2$ | = | 0.43 |
| $HMI/SiO_2$ | = | 0.35 |
| $H_2O/SiO_2$ | = | 19.4 | where R=hexamethyleneimine.

The mixture was crystallized in a stirred reactor at 150° C. for 4 days. The crystals were filtered, washed with water and dried at 120° C. A portion of the product was submitted for X-ray analysis and identified as the new crystalline material MCM-49. The material exhibited the X-ray powder diffraction pattern as shown in Table III and FIG. 1.

The chemical composition of the product was, in wt. %:

| | |
|---|---|
| N | 1.81 |
| Na | 0.38 |
| $Al_2O_3$ | 7.1 |
| $SiO_2$ | 72.8 |
| Ash | 79.2 |

The $SiO_2/Al_2O_3$ molar ratio of this product was 17.4.

The sorption capacities, after calcining for 6 hours at 538° C. were, in wt. %:

| | |
|---|---|
| Cyclohexane, 40 Torr | 4.4 |
| n-Hexane, 40 Torr | 12.8 |
| $H_2O$, 12 Torr | 11.1 |

A portion of the sample was calcined in air for 16 hours at 538° C. This material exhibited the X-ray diffraction pattern shown in Table IV.

TABLE III

| Degrees 2-Theta | Interplanar d-spacing (A) | $I/I_o$ |
|---|---|---|
| 3.2 | 27.5 | 11 |
| 6.75 | 13.09 | 36 sh |
| 7.08 | 12.49 | 100 |
| 7.88 | 11.23 | 40 |
| 9.81 | 9.02 | 24 |
| 12.79 | 6.92 | 13 |
| 13.42 | 6.60 | 5* |
| 13.87 | 6.38 | 6 |
| 14.24 | 6.22 | 7 |
| 14.64 | 6.05 | 4 |
| 15.24 | 5.81 | 2 |
| 15.81 | 5.61 | 8 |
| 17.72 | 5.01 | 2 |
| 18.91 | 4.69 | 4 |
| 19.27 | 4.61 | 5 |
| 20.09 | 4.42 | 19 |
| 20.83 | 4.26 | 6 |
| 21.48 | 4.14 | 15 |
| 21.78 | 4.08 | 29 |
| 22.22 | 4.00 | 12 |
| 22.59 | 3.94 | 36 |
| 23.56 | 3.78 | 19 |
| 24.87 | 3.58 | 21 |
| 25.10 | 3.55 | 6 |
| 25.89 | 3.44 | 80 |
| 26.32 | 3.39 | 7 |
| 26.81 | 3.33 | 17 |
| 27.57 | 3.24 | 11 |
| 28.36 | 3.15 | 7 |
| 29.03 | 3.08 | 3 |
| 29.50 | 3.03 | 2 |
| 31.47 | 2.842 | 3 |
| 32.16 | 2.784 | 3 |
| 33.26 | 2.694 | 6 |
| 34.08 | 2.631 | 2 |
| 34.83 | 2.576 | 1 |
| 36.25 | 2.478 | 2 |
| 36.96 | 2.432 | 2 |
| 37.72 | 2.385 | 7 | sh = Shoulder
* = Impurity peak

TABLE IV

| Degrees 2-Theta | Interplanar d-spacing (A) | $I/I_o$ |
|---|---|---|
| 3.4 | 26.0 | 6 |

TABLE IV-continued

| Degrees 2-Theta | Interplanar d-spacing (A) | I/I$_o$ |
|---|---|---|
| 6.96 | 12.69 | 45 sh |
| 7.15 | 12.37 | 100 |
| 7.97 | 11.09 | 58 |
| 9.97 | 8.87 | 49 |
| 12.88 | 6.88 | 10 |
| 13.50 | 6.56 | 3* |
| 14.34 | 6.18 | 26 |
| 14.76 | 6.00 | 8 |
| 15.30 | 5.79 | 1 |
| 15.96 | 5.55 | 13 |
| 17.84 | 4.97 | 1 |
| 19.03 | 4.66 | 3 |
| 19.34 | 4.59 | 2 |
| 19.67 | 4.51 | 2* |
| 20.26 | 4.38 | 10 |
| 21.18 | 4.20 | 3 |
| 21.59 | 4.12 | 10 |
| 21.88 | 4.06 | 17 |
| 22.40 | 3.97 | 8 |
| 22.72 | 3.91 | 28 |
| 23.74 | 3.75 | 16 |
| 24.73 | 3.60 | 3 |
| 24.98 | 3.57 | 10 |
| 25.23 | 3.53 | 5 |
| 26.00 | 3.43 | 57 |
| 26.98 | 3.30 | 12 |
| 27.81 | 3.21 | 12 |
| 28.64 | 3.12 | 7 |
| 29.14 | 3.06 | 2 |
| 29.69 | 3.01 | 2 |
| 31.62 | 2.830 | 3 |
| 32.28 | 2.773 | 3 |
| 33.38 | 2.685 | 6 |
| 34.43 | 2.605 | 2 |
| 34.98 | 2.565 | 2 |
| 36.39 | 2.469 | 1 |
| 37.09 | 2.424 | 2 |
| 37.86 | 2.377 | 4 | sh = Shoulder
* = Impurity peak

EXAMPLE 2

The calcined portion of the product of Example 1 was ammonium exchanged and calcined at 538° C. in air for 16 hours to provide the hydrogen form transformation product of the crystalline MCM-49. The Alpha Test proved this material to have an Alpha Value of 291.

EXAMPLE 3

A 1.45 part quantity of sodium aluminate was added to a solution containing 1 part of 50% NaOH solution and 53.1 parts H$_2$O. A 5.4 part quantity of HMI was added, followed by 10.3 parts of Ultrasil, a precipitated spray-dried silica (about 90% SiO$_2$). The reaction mixture was thoroughly mixed and transferred to a stainless steel autoclave equipped with a stirrer.

The reaction mixture had the following composition in mole ratios:

| | |
|---|---|
| SiO$_2$/Al$_2$O$_3$ | 25 |
| OH$^-$/SiO$_2$ | 0.19 |
| Na/SiO$_2$ | 0.19 |
| HMI/SiO$_2$ | 0.35 |
| H$_2$O/SiO$_2$ | 19.3 |

Figure 2:
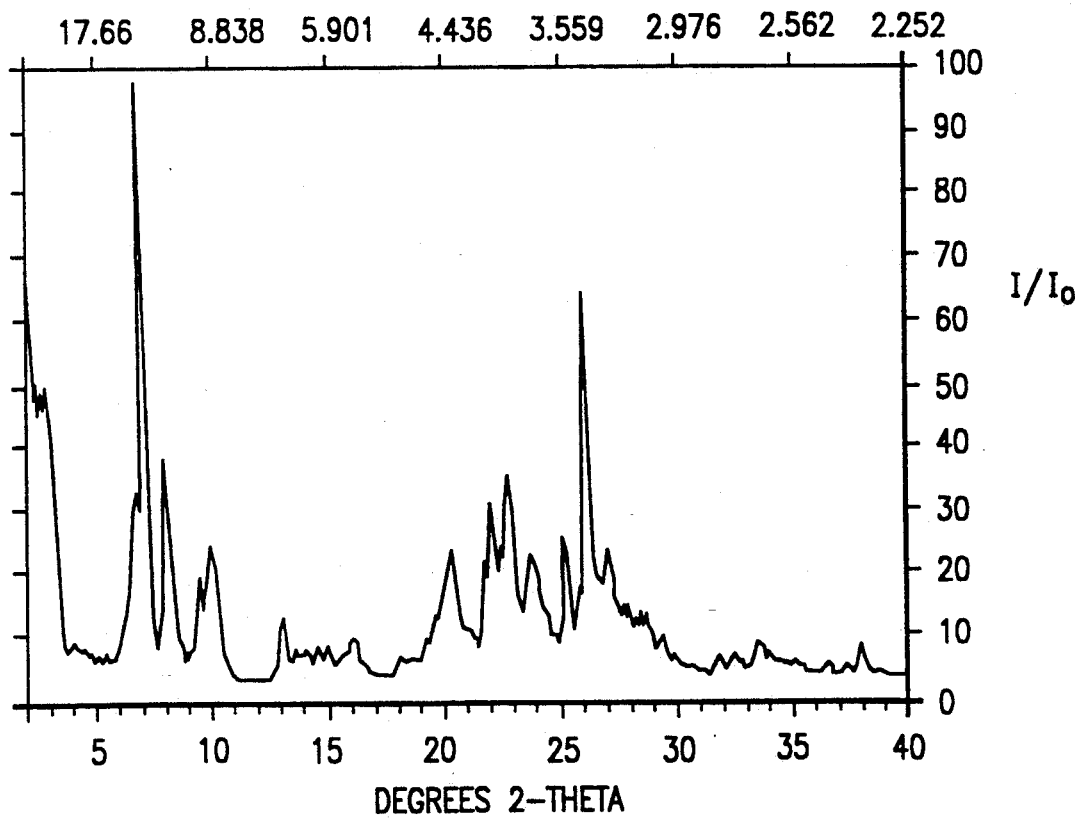

The mixture was crystallized with stirring at 150° C. for 8 days. The product was identified as MCM-49 and had the X-ray pattern which appears in Table V and FIG. 2.

The chemical composition of the product was, in wt. %:

| | |
|---|---|
| N | 2.29 |
| Na | 0.19 |
| Al$_2$O$_3$ | 6.3 |
| SiO$_2$ | 71.0 |
| Ash | 77.9 |

The silica/alumina mole ratio of the product was 19.2.

The sorption capacities, after calcining for 16 hours at 538° C. were, in wt. %:

| | |
|---|---|
| Cyclohexane, 40 Torr | 9.9 |
| n-Hexane, 40 Torr | 14.6 |
| H$_2$O, 12 Torr | 15.1 |

A portion of the sample was calcined in air for 16 hours at 538° C. This material exhibited the X-ray diffraction pattern shown in Table VI.

TABLE V

| Degrees 2-Theta | Interplanar d-spacing (A) | I/I$_o$ |
|---|---|---|
| 3.0 | 29.3 | 8 |
| 3.9 | 22.8 | 2+ |
| 6.66 | 13.27 | 34 |
| 7.10 | 12.45 | 100 |
| 7.91 | 11.18 | 39 |
| 9.24 | 9.57 | 16* |
| 9.79 | 9.04 | 23 |
| 12.79 | 6.92 | 11 |
| 13.60 | 6.51 | 5 |
| 14.28 | 6.20 | 5 |
| 14.68 | 6.03 | 5 |
| 15.33 | 5.78 | 2 |
| 15.83 | 5.60 | 7 |
| 17.80 | 4.98 | 2 |
| 18.94 | 4.68 | 3 |
| 19.32 | 4.59 | 8 |
| 20.09 | 4.42 | 21 |
| 21.51 | 4.13 | 17 |
| 21.82 | 4.07 | 27 |
| 22.17 | 4.01 | 13 |
| 22.58 | 3.94 | 33 |
| 23.50 | 3.79 | 19 |
| 24.09 | 3.69 | 8* |
| 24.96 | 3.57 | 23 |
| 25.55 | 3.49 | 11* |
| 25.93 | 3.44 | 73 |
| 26.82 | 3.32 | 20 |
| 27.54 | 3.24 | 9 |
| 28.32 | 3.15 | 9** |
| 29.07 | 3.07 | 5** |
| 31.50 | 2.840 | 3 |
| 32.15 | 2.784 | 3 |
| 33.31 | 2.690 | 6 |
| 34.48 | 2.601 | 2 |
| 36.26 | 2.478 | 2 |
| 37.03 | 2.428 | 2 |
| 37.75 | 2.383 | 6 |

+ = Non-crystallographic MCM-49 peak
* = Impurity peak
** = May contain impurity peak

TABLE VI

| Degrees 2-Theta | Interplanar d-spacing (A) | I/I$_o$ |
|---|---|---|
| 3.9 | 22.8 | 6+ |
| 6.88 | 12.84 | 46 sh |
| 7.11 | 12.43 | 100 |
| 7.97 | 11.10 | 57 |
| 9.35 | 9.46 | 25* |
| 9.94 | 8.90 | 48 |
| 12.53 | 7.07 | 4* |
| 12.82 | 6.90 | 13 |

TABLE VI-continued

| Degrees 2-Theta | Interplanar d-spacing (A) | I/I$_o$ |
|---|---|---|
| 13.41 | 6.60 | 3* |
| 14.30 | 6.19 | 36 |
| 14.73 | 6.01 | 6 |
| 15.93 | 5.56 | 10 |
| 17.90 | 4.96 | 2 |
| 18.98 | 4.68 | 3 |
| 19.34 | 4.59 | 3 |
| 20.18 | 4.40 | 11 |
| 21.56 | 4.12 | 11 |
| 21.86 | 4.07 | 18 |
| 22.34 | 3.98 | 10 |
| 22.67 | 3.92 | 30 |
| 23.68 | 3.76 | 17 |
| 24.94 | 3.57 | 15 |
| 25.20 | 3.53 | 6* |
| 25.97 | 3.43 | 60 |
| 26.93 | 3.31 | 13 |
| 27.79 | 3.21 | 11 |
| 28.56 | 3.13 | 8** |
| 29.10 | 3.07 | 3** |
| 29.60 | 3.02 | 1 |
| 31.58 | 2.83 | 3 |
| 32.24 | 2.776 | 3 |
| 33.34 | 2.688 | 7 |
| 34.59 | 2.593 | 3 |
| 36.33 | 2.473 | 1 |
| 37.05 | 2.426 | 2 |
| 37.79 | 2.380 | 4 | sh = Shoulder
+ = Non-crystallographic MCM-49 peak
* = Impurity peak
** = May contain impurity peak

EXAMPLE 4

The calcined portion of the product of Example 3 was ammonium exchanged and calcined at 538° C. in air for 16 hours to provide the hydrogen form transformation product of the crystalline MCM-49. The Alpha Test proved this material to have an Alpha Value of 286.

EXAMPLE 5

A 10.5 part quantity of gallium oxide was added to a solution containing 1.0 part sodium aluminate, 3.05 parts 50% NaOH solution and 280 parts H$_2$O. A 25.6 part quantity of HMI was added followed by 56.6 parts of Ultrasil and 1.7 parts of MCM-22 seeds. The slurry was thoroughly mixed.

The composition of the reaction mixture in mole ratios:

| | | |
|---|---|---|
| SiO$_2$/Al$_2$O$_3$ | = | 200 |
| SiO$_2$/Ga$_2$O$_3$ | = | 15.2 |
| OH$^-$/SiO$_2$ | = | 0.057 |
| Na/SiO$_2$ | = | 0.057 |
| HMI/SiO$_2$ | = | 0.30 |
| H$_2$O/SiO$_2$ | = | 18.4 |

Figure 3:
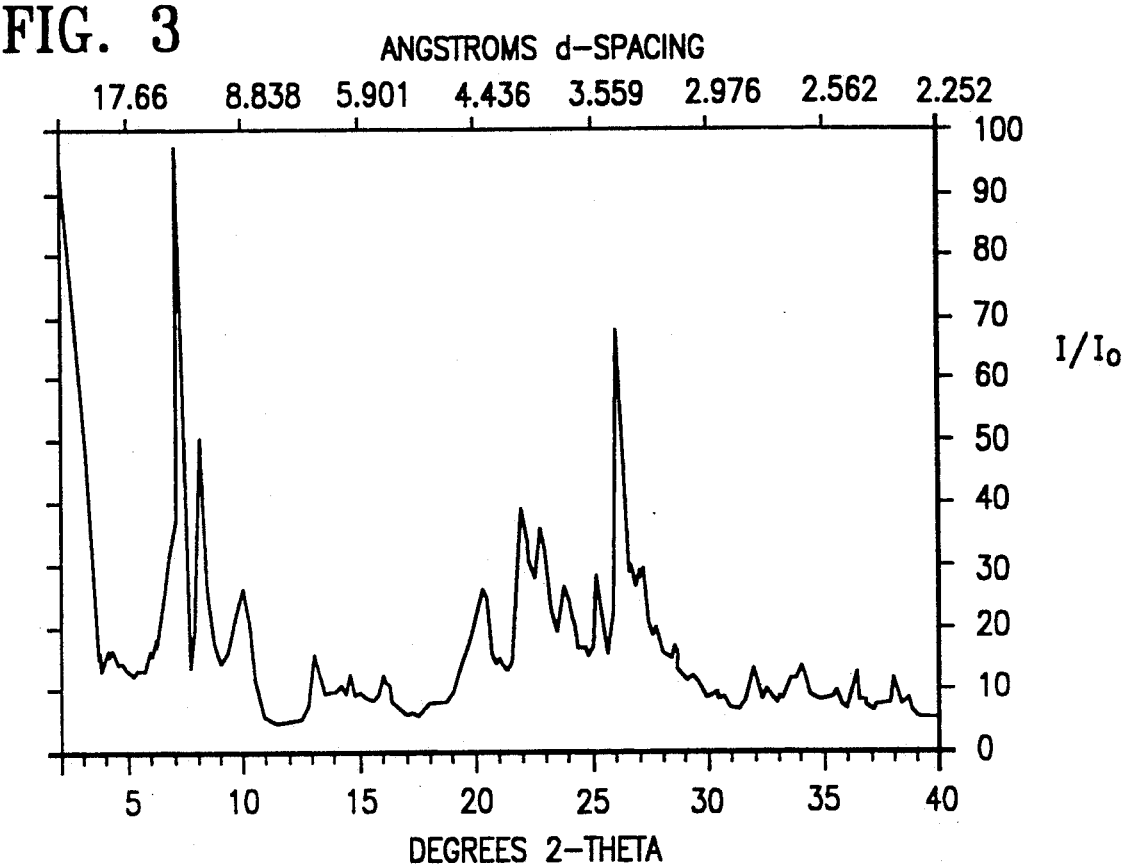

The mixture was crystallized with stirring at 150° C. for 10 days. The product was identified as MCM-49 and had the X-ray pattern which appears in Table VII and FIG. 3.

The chemical composition of the product was, in wt. %:

| | |
|---|---|
| N | 1.89 |
| Na | 0.40 |
| Ga | 8.5 |
| Al$_2$O$_3$ | 0.81 |
| SiO$_2$ | 65.6 |
| Ash | 79.3 | with silica/alumina and silica/gallia molar ratios for the product of:

| | |
|---|---|
| SiO$_2$/Al$_2$O$_3$ | 138 |
| SiO$_2$/Ga$_2$O$_3$ | 17.9 |

The sorption capacities, after calcining for 3 hours at 538° C. were, in wt. %:

| | |
|---|---|
| Cyclohexane, 40 Torr | 13.3 |
| n-Hexane, 40 Torr | 11.3 |
| H$_2$O, 12 Torr | 12.3 |

A portion of the sample was calcined in air for 16 hours at 538° C. This material exhibited the X-ray diffraction pattern shown in Table VIII.

TABLE VII

| Degrees 2-Theta | Interplanar d-spacing (A) | I/I$_o$ |
|---|---|---|
| 3.9 | 22.8 | 6+ |
| 6.66 | 13.27 | 30 sh |
| 7.08 | 12.48 | 100 |
| 7.92 | 11.17 | 43 |
| 9.27 | 9.54 | 8* |
| 9.74 | 9.08 | 20 |
| 12.78 | 6.93 | 12 |
| 13.75 | 6.44 | 6 |
| 14.28 | 6.20 | 5 |
| 14.62 | 6.06 | 3 |
| 15.78 | 5.62 | 8 |
| 17.99 | 4.93 | 3 |
| 18.92 | 4.69 | 6 |
| 20.10 | 4.42 | 24 |
| 20.86 | 4.26 | 9 |
| 21.47 | 4.14 | 10 |
| 21.73 | 4.09 | 26 |
| 22.57 | 3.94 | 29 |
| 23.53 | 3.78 | 22 |
| 24.92 | 3.57 | 24 |
| 25.91 | 3.44 | 82 |
| 26.80 | 3.33 | 19 |
| 27.43 | 3.25 | 14 |
| 28.31 | 3.15 | 10 |
| 29.04 | 3.07 | 5 |
| 31.59 | 2.832 | 8 |
| 32.17 | 2.783 | 3 |
| 33.25 | 2.694 | 6 |
| 33.70 | 2.659 | 8* |
| 35.12 | 2.555 | 4* |
| 35.96 | 2.497 | 11* |
| 36.29 | 2.476 | 4 |
| 37.73 | 2.384 | 7 | sh = Shoulder
+ = Non-crystallographic MCM-49 peak
* = Impurity peak

TABLE VIII

| Degrees 2-Theta | Interplanar d-spacing (A) | I/I$_o$ |
|---|---|---|
| 3.9 | 22.8 | 11+ |
| 6.89 | 12.83 | 40 sh |
| 7.11 | 12.43 | 100 |
| 7.96 | 11.11 | 55 |
| 9.40 | 9.41 | 10* |
| 9.94 | 8.90 | 47 |
| 12.81 | 6.91 | 10 |
| 14.31 | 6.19 | 32 |
| 14.74 | 6.01 | 4 |
| 15.94 | 5.56 | 12 |

TABLE VIII-continued

| Degrees 2-Theta | Interplanar d-spacing (A) | I/I$_o$ |
|---|---|---|
| 17.89 | 4.96 | <1 |
| 19.00 | 4.67 | 3 |
| 19.39 | 4.58 | 3 |
| 20.22 | 4.39 | 9 |
| 21.56 | 4.12 | 9 |
| 21.86 | 4.07 | 17 |
| 22.70 | 3.92 | 29 |
| 23.70 | 3.75 | 16 |
| 24.99 | 3.56 | 14 |
| 26.01 | 3.43 | 57 |
| 26.96 | 3.31 | 12 |
| 27.84 | 3.20 | 10 |
| 28.60 | 3.12 | 5 |
| 29.10 | 3.07 | 3 |
| 31.63 | 2.829 | 6 |
| 32.28 | 2.773 | 3 |
| 33.39 | 2.684 | 7 |
| 33.72 | 2.658 | 9* |
| 35.07 | 2.559 | 4* |
| 35.94 | 2.499 | 4* |
| 36.40 | 2.468 | 1 |
| 37.13 | 2.422 | 2 |
| 37.88 | 2.375 | 3 | sh = Shoulder
+ = Non-crystallographic MCM-49 peak
* = Impurity peak

EXAMPLE 6

The calcined portion of the product of Example 5 was ammonium exchanged and calcined at 538° C. in air for 16 hours to provide the hydrogen form transformation product of the crystalline MCM-49. The Alpha Test proved this material to have an Alpha Value of 64.

EXAMPLE 7

A solution containing 1 part of Al$_2$(SO$_4$)$_3$ xH$_2$O, 1.31 parts of 50% NaOH solution and 14.0 parts of H$_2$O was prepared. To this were added 2.8 parts of Ultrasil precipitated silica followed by 1.48 parts of HMI. The reaction mixture was thoroughly mixed. The composition of the reaction mixture in mole ratios was:

| | | |
|---|---|---|
| SiO$_2$/Al$_2$O$_3$ | = | 25.5 |
| OH$^-$/SiO$_2$ | = | 0.15 |
| Na/SiO$_2$ | = | 0.39 |
| HMI/SiO$_2$ | = | 0.35 |
| H$_2$O/SiO$_2$ | = | 19.4 |

Figure 4:
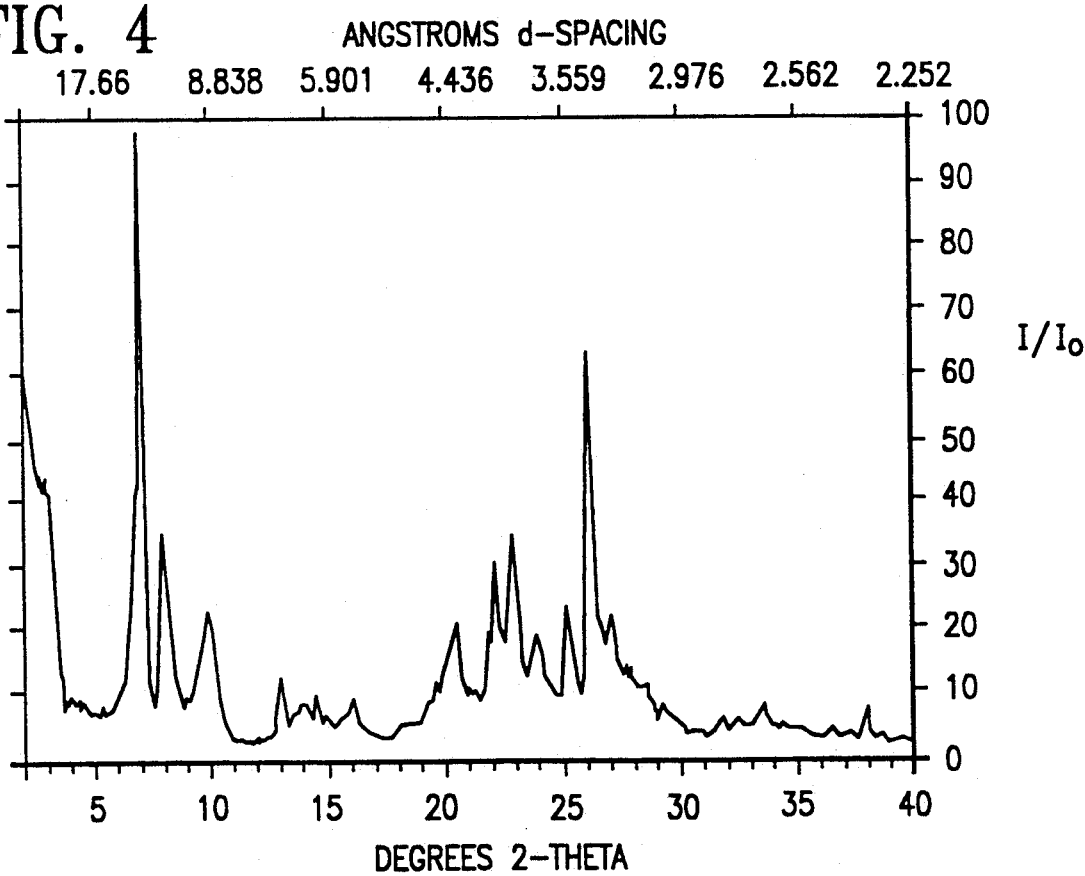

The mixture was crystallized for 5 days at 143° C. The product was washed, dried at 120° C. and identified by X-ray analysis as MCM-49. It exhibited an X-ray pattern as shown in Table IX and FIG. 4.

The sorption capacities, after calcining for 16 hours at 538° C. were, in wt. %:

| | |
|---|---|
| Cyclohexane, 40 Torr | 8.8 |
| n-Hexane, 40 Torr | 15.9 |
| H$_2$O, 12 Torr | 13.6 |

The chemical composition of the product was, in wt. %:

| | |
|---|---|
| N | 1.83 |
| Na | 0.27 |
| Al$_2$O$_3$ | 6.8 |
| SiO$_2$ | 73.8 |
| Ash | 80.5 |

The silica/alumina mole ratio of the product was 18.4.
The surface area of this material was measured to be 459 m$^2$/g.

A portion of the sample was calcined in air for 16 hours at 538° C. This material exhibited the X-ray diffraction pattern shown in Table X.

TABLE IX

| Degrees 2-Theta | Interplanar d-spacing (A) | I/I$_o$ |
|---|---|---|
| 3.1 | 28.5 | 17 |
| 4.0 | 22.2 | 3+ |
| 6.73 | 13.14 | 43 sh |
| 7.08 | 12.48 | 100 |
| 7.92 | 11.16 | 42 |
| 9.69 | 9.13 | 23 |
| 12.80 | 6.91 | 13 |
| 13.76 | 6.44 | 7 |
| 14.27 | 6.20 | 6 |
| 14.65 | 6.05 | 3 |
| 15.85 | 5.59 | 7 |
| 17.82 | 4.98 | 2 |
| 18.92 | 4.69 | 3 |
| 19.32 | 4.59 | 8 |
| 20.13 | 4.41 | 20 |
| 21.48 | 4.14 | 12 |
| 21.82 | 4.07 | 31 |
| 22.56 | 3.94 | 36 |
| 23.59 | 3.77 | 18 |
| 24.91 | 3.57 | 22 |
| 25.91 | 3.44 | 79 |
| 26.74 | 3.33 | 20 |
| 27.61 | 3.23 | 7 |
| 28.25 | 3.16 | 8 |
| 29.14 | 3.06 | 3 |
| 31.48 | 2.842 | 3 |
| 32.16 | 2.783 | 3 |
| 33.26 | 2.694 | 6 |
| 33.85 | 2.648 | 3 sh |
| 34.72 | 2.584 | 2 |
| 36.26 | 2.478 | 2 |
| 37.00 | 2.429 | 2 |
| 37.73 | 2.384 | 7 | sh = Shoulder
+ = Non-crystallographic MCM-49 peak

TABLE X

| Degrees 2-Theta | Interplanar d-spacing (A) | I/I$_o$ |
|---|---|---|
| 3.9 | 22.8 | 6+ |
| 6.91 | 12.79 | 38 sh |
| 7.12 | 12.42 | 100 |
| 7.96 | 11.10 | 53 |
| 9.94 | 8.90 | 39 |
| 12.84 | 6.90 | 11 |
| 14.30 | 6.19 | 39 |
| 14.71 | 6.02 | 10 |
| 15.92 | 5.57 | 12 |
| 18.00 | 4.93 | 1 |
| 18.98 | 4.67 | 3 |
| 19.34 | 4.59 | 3 |
| 20.17 | 4.40 | 10 |
| 21.55 | 4.12 | 10 |
| 21.86 | 4.07 | 17 |
| 22.67 | 3.92 | 27 |
| 23.69 | 3.75 | 15 |
| 24.96 | 3.57 | 13 |
| 25.98 | 3.43 | 61 |
| 26.93 | 3.31 | 13 |
| 27.80 | 3.21 | 9 |
| 28.58 | 3.12 | 6 |
| 29.11 | 3.07 | 2 |
| 29.63 | 3.02 | 1 |
| 31.57 | 2.834 | 3 |
| 32.23 | 2.777 | 3 |

TABLE X-continued

| Degrees 2-Theta | Interplanar d-spacing (A) | I/I₀ |
|---|---|---|
| 33.35 | 2.687 | 6 |
| 34.60 | 2.593 | 3 |
| 36.34 | 2.472 | 1 |
| 37.06 | 2.426 | 1 |
| 37.83 | 2.378 | 5 | sh = Shoulder
+ = Non-crystallographic MCM-49 peak

EXAMPLE 8

A 2.24 part quantity of 45% sodium aluminate was added to a solution containing 1.0 part of 50% NaOH solution and 43.0 parts $H_2O$ in an autoclave. An 8.57 part quantity of Ultrasil precipitated silica was added with agitation, followed by 4.51 parts of HMI.

The reaction mixture had the following composition, in mole ratios:

| | | |
|---|---|---|
| $SiO_2/Al_2O_3$ | = | 23 |
| $OH^-/SiO_2$ | = | 0.21 |
| $Na/SiO_2$ | = | 0.21 |
| $HMI/SiO_2$ | = | 0.35 |
| $H_2O/SiO_2$ | = | 19.3 |

Figure 5:
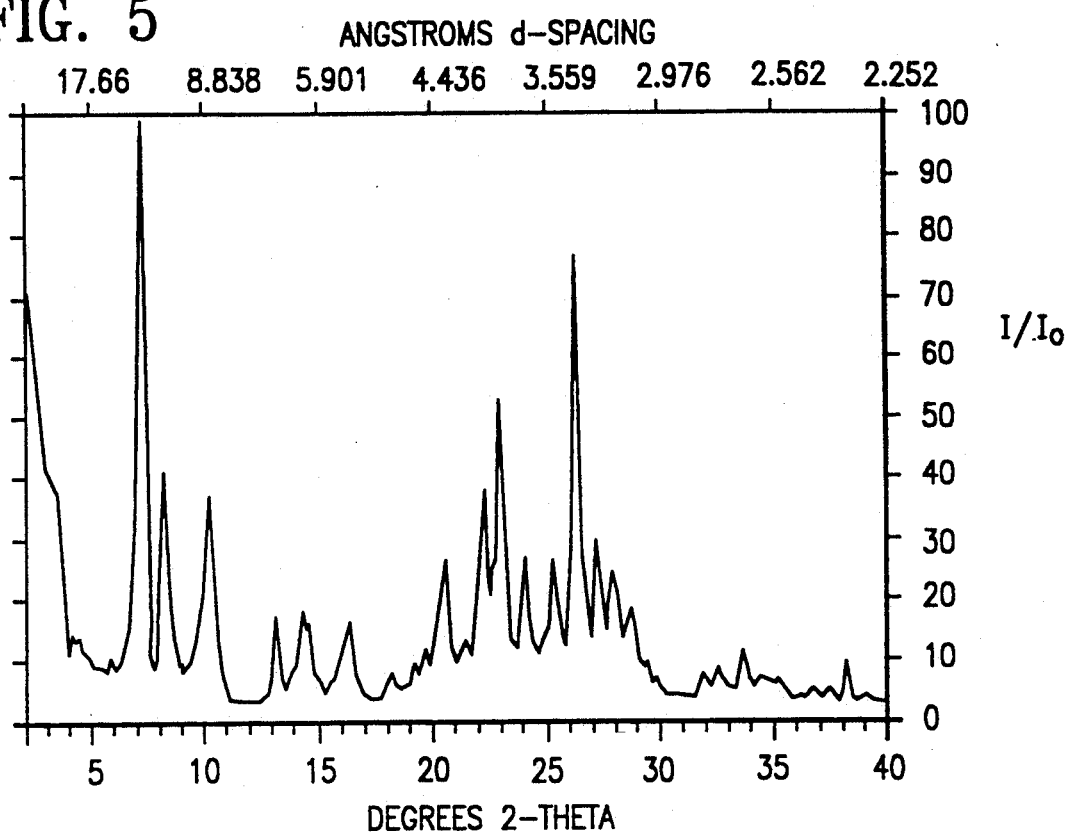

The mixture was crystallized at 150° C. for 84 hours with stirring. The product was identified as MCM-49 and had the X-ray pattern which appears in Table XI and FIG. 5.

The chemical composition of the product was, in wt. %:

| | |
|---|---|
| N | 1.70 |
| Na | 0.70 |
| $Al_2O_3$ | 7.3 |
| $SiO_2$ | 74.5 |
| Ash | 84.2 |

The silica/alumina mole ratio of the product was 17.3.

The sorption capacities, after calcining at 538° C. for 9 hours were, in wt. %:

| | |
|---|---|
| Cyclohexane, 40 Torr | 10.0 |
| n-Hexane, 40 Torr | 13.1 |
| $H_2O$, 12 Torr | 15.4 |

A portion of the sample was calcined in air for 3 hours at 538° C. This material exhibited the X-ray diffraction pattern shown in Table XII.

TABLE XI

| Degrees 2-Theta | Interplanar d-spacing (A) | I/I₀ |
|---|---|---|
| 3.1 | 28.5 | 18 |
| 3.9 | 22.8 | 7+ |
| 6.81 | 12.99 | 61 sh |
| 7.04 | 12.55 | 97 |
| 7.89 | 11.21 | 41 |
| 9.80 | 9.03 | 40 |
| 12.76 | 6.94 | 17 |
| 13.42 | 6.60 | 4* |
| 13.92 | 6.36 | 17 |
| 14.22 | 6.23 | 11 |
| 14.63 | 6.05 | 2 |
| 15.81 | 5.61 | 15 |
| 17.71 | 5.01 | 4 |
| 18.86 | 4.71 | 4 |
| 19.23 | 4.62 | 6 |
| 20.09 | 4.42 | 27 |
| 20.93 | 4.24 | 8 |
| 21.44 | 4.14 | 17 |
| 21.74 | 4.09 | 37 |
| 22.16 | 4.01 | 17 |
| 22.56 | 3.94 | 58 |
| 3.53 | 3.78 | 26 |
| 24.83 | 3.59 | 22 |
| 25.08 | 3.55 | 10 |
| 25.86 | 3.45 | 100 |
| 26.80 | 3.33 | 28 |
| 27.53 | 3.24 | 21 |
| 28.33 | 3.15 | 15 |
| 28.98 | 3.08 | 4 |
| 29.47 | 3.03 | 2 |
| 31.46 | 2.843 | 4 |
| 32.08 | 2.790 | 6 |
| 33.19 | 2.699 | 9 |
| 34.05 | 2.633 | 5 |
| 34.77 | 2.580 | 4 |
| 36.21 | 2.481 | 2 |
| 36.90 | 2.436 | 3 |
| 37.68 | 2.387 | 8 | sh = Shoulder
+ = Non-crystallographic MCM-49 peak
* = Impurity peak

TABLE XII

| Degrees 2-Theta | Interplanar d-spacing (A) | I/I₀ |
|---|---|---|
| 3.2 | 28.0 | 9+ |
| 3.9 | 22.8 | 7+ |
| 6.90 | 12.81 | 48 sh |
| 7.13 | 12.39 | 100 |
| 7.98 | 11.08 | 46 |
| 9.95 | 8.89 | 53 |
| 12.87 | 6.88 | 10 |
| 14.32 | 6.18 | 36 |
| 14.74 | 6.01 | 11 |
| 15.94 | 5.56 | 17 |
| 17.87 | 4.96 | 2 |
| 19.00 | 4.67 | 5 |
| 19.35 | 4.59 | 3 |
| 20.24 | 4.39 | 14 |
| 21.06 | 4.22 | 5 |
| 21.56 | 4.12 | 15 |
| 21.87 | 4.06 | 25 |
| 22.32 | 3.98 | 12 |
| 22.69 | 3.92 | 41 |
| 23.69 | 3.76 | 23 |
| 24.95 | 3.57 | 19 |
| 25.22 | 3.53 | 4 |
| 25.99 | 3.43 | 90 |
| 26.94 | 3.31 | 20 |
| 27.73 | 3.22 | 17 |
| 28.55 | 3.13 | 11 |
| 29.11 | 3.07 | 3 |
| 29.63 | 3.01 | 2 |
| 31.59 | 2.833 | 6 |
| 32.23 | 2.777 | 4 |
| 33.34 | 2.687 | 9 |
| 34.35 | 2.611 | 4 |
| 34.92 | 2.570 | 3 |
| 36.35 | 2.471 | 2 |
| 37.07 | 2.425 | 2 |
| 37.82 | 2.379 | 6 | sh = Shoulder
+ = Non-crystallographic MCM-49 peak

EXAMPLE 9

The calcined portion of the product of Example 8 was ammonium exchanged and calcined at 538° C. in air for 3 hours to provide the hydrogen form transformation product of the crystalline MCM-49. The Alpha Test proved this material to have an Alpha Value of 308.

EXAMPLE 10

Synthetic crystalline MCM-49 was prepared by charging 43.0 parts of $H_2O$ and 1.0 part of NaOH solution (50% by weight) to an autoclave, followed by 2.2 parts of sodium aluminate solution (45% by weight). After mixing thoroughly, 8.6 parts of Nasilco's Ultrasil VN3SP and 4.5 parts of hexamethyleneimine were added and mixed thoroughly. The autoclave was heated to 150° C. with stirring and maintained at these conditions until crystalization was complete. The product was identified as MCM-49 by X-ray diffraction. After flashing the hexamethyleneimine, the slurry was cooled, washed, filtered, and dried. MCM-49 composite catalyst was prepared by combining one part of dried MCM-49 crystalline material with 0.54 part of La Roche Versal brand alumina. The mix was mulled and extruded to form 1/16 inch pellets which were dried at 120° C. The pellets were then calcined in flowing nitrogen for 6 hours at 480° C. The cooled catalyst was exchanged with 1N $NH_4NO_3$ (5 cc/g catalyst) at room temperature for one hour and then washed with water. The exchange was repeated two more times. The catalyst was then dried at 120° C. The exchanged extrudates were calcined in flowing air at 538° C. for 12 hours. The calcined material was found to have an Alpha value of 254.

Sorption capacities of the calcined catalyst are shown below in weight percent.

| | |
|---|---|
| Cyclohexane, 40 Torr: | 12.1 |
| n-Hexane, 40 Torr: | 12.2 |
| $H_2O$, 12 Torr: | 16.8. |

EXAMPLE 11

Synthetic crystalline material MCM-22 was prepared by charging 43.5 parts of $H_2O$ and 1.0 part of NaOH solution (50% by weight) to an autoclave, followed by 1.7 parts of sodium aluminate solution (45% by weight). After mixing thoroughly, 8.6 parts of Nasilco's Ultrasil VN3SP and 4.5 parts of hexamethyleneimine were added and mixed thoroughly. The autoclave was heated to 143° C. while stirring and was maintained at these conditions until crystallization was complete. The product was identified as MCM-22 by X-ray diffraction. After flashing the hexamethyleneimine, the slurry was cooled, washed, filtered, and dried. MCM-22 composite catalyst was prepared from one part of the dried MCM-22 zeolite crystals and 0.54 part of Kaiser SA alumina. The MCM-22 and alumina mix was mulled and extruded to form 1/16 inch pellets which were dried at 120° C. The extruded pellets were then calcined in flowing nitrogen for 3 hours at 480° C. and in air for 6 hours at 538° C. The catalyst was cooled down and exchanged with 1N $NH_4NO_3$ at room temperature for two hours. The exchange was repeated two more times and then washed with water. The exchanged extrudates were dried at 120° C. and then calcined in flowing air at 538° C. for 3 hours.

EXAMPLES 12-17

Examples 12-17 were carried out in a fixed bed reactor using a 50:1 wt.:wt. mixed isobutane:2-butene feed. The activity and product selectivity were monitored by gas chromatographic analysis of the off-gas and liquid product using a fused silica capillary column (Alltech's Durabond DB-1).

The isobutane and isobutane/olefin feeds (both C.P. Grade) were all obtained from Matheson Chemical Company and used without further purification.

The experiments using the MCM-22 catalyst of Example 11 (Examples 15-17) and the MCM-49 catalyst of Example 10 (Examples 12-14) were conducted at 300° F. and 500 psig. Both catalysts were crushed to 30/60 mesh size prior to charging to the fixed bed reactor. The weight hourly space velocity (based on catalyst) for Examples 12-17 was 0.045 $hr^{-1}$.

Figure 6:
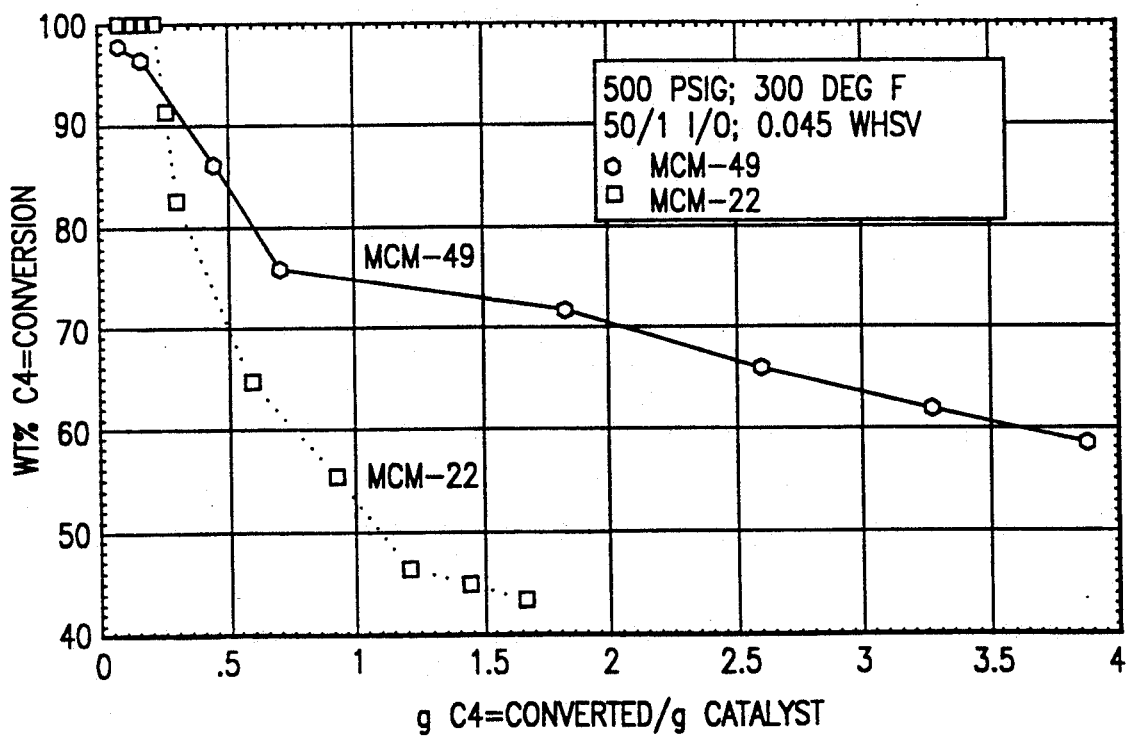
FIG. 6 compares the isoparaffin:olefin alkylation performance of an MCM-22 catalyst with that of isoparaffin:olefin alkylation performance of an MCM-49 catalyst of the present invention, showing weight percent $C_4$ olefin conversion as a function of grams $C_4$ olefin converted per gram of catalyst.

The data contained in Table XIII and in FIG. 6 clearly demonstrate the improvement in catalyst stability shown by the catalyst of the present invention. Table XIII compares the performance of the MCM-49 catalyst with that of the MCM-22 catalyst. The MCM-49 catalyst showed superior stability while providing comparable product yield and quality to that of MCM-22 catalyst (as measured both by the ratio of high octane trimethylpentanes (TMP) to low octane dimethylhexanes (DMH) and by the $C_{9+}$ yield). For example at 59 hours on stream (HOS) (1.8 g $C_4$=conv/g catalyst), MCM-49 gave >70% $C_4$=conversion while with MCM-22, at 64 HOS (1.7 g $C_4$=conv/g catalyst), the $C_4$=conversion dropped to <45%. With MCM-49, the $C_4$=conversion was 58% even at 128 HOS (3.9 g $C_4$=conv/g catalyst).

TABLE XIII

Fixed-Bed Alkylation: Comparison of Alumina-bound MCM-22 and MCM-49 Catalysts

| | MCM-49/$Al_2O_3$ | | | MCM-22/$Al_2O_3$ | | |
|---|---|---|---|---|---|---|
| Catalyst | Ex. 12 | Ex. 13 | Ex. 14 | Ex. 15 | Ex. 16 | Ex. 17 |
| Reaction Conditions | | | | | | |
| I/O Feed: | 50/1 | 50/1 | 50/1 | 50/1 | 50/1 | 50/1 |
| R × R Pressure (psig) | 500 | 500 | 500 | 500 | 500 | 500 |
| R × R Temp. (°F.) | 300 | 300 | 300 | 300 | 300 | 300 |
| Time on Stream (hrs) | 11 | 59 | 128 | 5 | 16 | 64 |
| $C_4$ = WHSV ($hr^{-1}$) | .046 | .042 | .046 | .046 | .046 | .040 |
| $C_4$ = Conv. (wt %) | 86.2 | 71.9 | 58.3 | 100 | 64.7 | 43.4 |
| Grams $C_4$ olefin converted per gram of catalyst | 0.46 | 1.83 | 3.89 | 0.23 | 0.59 | 1.67 |
| $C_5$ + yield, grams $C_5$ + per gram of olefin converted | 1.6 | 1.7 | 1.5 | 1.4 | 1.6 | 1.7 |
| $C_5$ + Analysis (weight percent): | | | | | | |
| $C_5$—$C_7$ | 25.8 | 20.0 | 18.0 | 34.4 | 21.7 | 19.8 |
| Total $C_8$ | 60.3 | 64.7 | 67.7 | 56.9 | 60.6 | 66.0 |
| Total TMP | 41.9 | 41.1 | 35.7 | 37.6 | 37.4 | 33.6 |
| Total DMH | 13.2 | 13.0 | 13.0 | 15.3 | 12.3 | 12.0 |
| Total Unknown $C_8$ | 5.2 | 10.6 | 19.0 | 4.1 | 10.9 | 20.4 |
| 225-TMH | 0.7 | 0.7 | 0.5 | 1.0 | 0.8 | 0.6 |
| $C_{9+}$ | 13.6 | 15.3 | 14.2 | 8.7 | 17.9 | 14.9 |
| $C_8$ Composition (Weight percent): | | | | | | |
| TMP | 69.6 | 63.6 | 52.8 | 66.0 | 61.7 | 51.0 |

TABLE XIII-continued

Fixed-Bed Alkylation: Comparison of Alumina-bound MCM-22 and MCM-49 Catalysts

| Catalyst | MCM-49/Al$_2$O$_3$ | | | MCM-22/Al$_2$O$_3$ | | |
|---|---|---|---|---|---|---|
| | Ex. 12 | Ex. 13 | Ex. 14 | Ex. 15 | Ex. 16 | Ex. 17 |
| DMH | 21.8 | 20.0 | 19.2 | 26.9 | 20.3 | 18.1 |
| Unk C$_8$ | 8.6 | 16.4 | 28.1 | 7.2 | 18.0 | 30.9 |
| TMP/DMH | 3.2 | 3.2 | 2.8 | 2.5 | 3.0 | 2.8 |

Changes and modifications in the specifically described embodiments can be carried out without departing from the scope of the invention which is intended to be limited only by the scope of the appended claims.

What is claimed is:

1. An isoparaffin:olefin alkylation process comprising contacting isoparaffin and olefin with a calcined synthetic porous crystalline material which is characterized, in its uncalcined form, by an X-ray diffraction pattern including values as set forth in Table I of the specification and having a composition comprising the molar relationship $$X_2O_3:(n)YO_2,$$

wherein n is less than about 20, X is a trivalent element selected from the group consisting of aluminum, boron, iron, and gallium and Y is a tetravalent element selected from the group consisting of silicon and germanium.

2. The process of claim 1 wherein said synthetic porous crystalline material which is characterized, in its uncalcined form, by an X-ray diffraction pattern including values as set forth in Table III of the specification.

3. The process of claim 1 wherein said synthetic porous crystalline material which is characterized, in its uncalcined form, by an X-ray diffraction pattern including values as set forth in Table V of the specification.

4. The process of claim 1 wherein said synthetic porous crystalline material which is characterized, in its uncalcined form, by an X-ray diffraction pattern including values as set forth in Table VII of the specification.

5. The process of claim 1 wherein said synthetic porous crystalline material which is characterized, in its uncalcined form, by an X-ray diffraction pattern including values as set forth in Table IX of the specification.

6. The process of claim 1 wherein said synthetic porous crystalline material is characterized, in its uncalcined form, by an X-ray diffraction pattern including values as set forth in Table XI of the specification.

7. The process of claim 1 wherein said crystalline material has a composition characterized by values of n ranging from about 5 to less than about 20.

8. The process of claim 1 wherein said crystalline material has a composition characterized by values of n ranging from about 10 to about 19.

9. The process of claim 1 wherein said crystalline material has a composition, on an anhydrous basis and in terms of moles of oxides per n moles of YO$_2$, expressed by the formula:

$$(0.1-0.6)M_2O:(1-4)R:X_2O_3:nYO_2$$

wherein M is alkali or alkaline earth metal and R is an organic moiety.

10. The process of claim 9 wherein said R is hexamethyleneimine.

11. The process of claim 9 wherein original cations of the crystalline material are replaced, at least in part, with a cation or a mixture of cations selected from the group consisting of hydrogen and hydrogen precursors, rare earth metals, and metals of Groups IIA, IIIA, IVA, IB, IIB, IIIB, IVB, VIB and VIII of the Periodic Table of the Elements.

12. The process of claim 1 wherein X comprises aluminum and Y comprises silicon.

13. The process of claim 1 wherein X comprises gallium and Y comprises silicon.

14. The process of claim 7 wherein X comprises aluminum and Y comprises silicon.

15. The process of claim 7 wherein X comprises gallium and Y comprises silicon.

16. The process of claim 8 wherein X comprises aluminum and Y comprises silicon.

17. The process of claim 11 wherein said replacing cations comprise hydrogen or a hydrogen precursor.

18. The process of claim 11 wherein said replacing cations comprise metals.

19. A process of claim 1 wherein said crystalline material is composited in a matrix.

20. The process of claim 19 wherein said matrix comprises alumina, silica, zirconia, titania, magnesia, or beryllia or a combination thereof.

21. The process of claim 1 wherein said synthetic porous crystalline material has a bulk ratio of SiO$_2$:Al$_2$O$_3$ of less than about 20.

22. A process for alkylating an isoparaffin with an olefin comprising contacting an isoparaffin having from 4 to 8 carbon atoms with an olefin having from 2 to 12 carbon atoms in an alkylation reaction zone at temperature from about −20° C. to about 400° C. and pressures from subatmospheric to about 5000 psig with a calcined synthetic porous crystalline material which is characterized, in its uncalcined form, by an X-ray diffraction pattern including values as set forth in Table I of the specification and having a composition comprising the molar relationship $$X_2O_3:(n)YO_2,$$

wherein n is less than about 20, X is a trivalent element selected from the group consisting of aluminum, boron, iron, and gallium and Y is a tetravalent element selected from the group consisting of silicon and germanium wherein the molar ration of said isoparaffin to said olefin is from about 1:1 to about 250:1 to evolve a product stream containing C$_5$+ alkylate.

* * * * *